United States Patent [19]
Braun et al.

[11] 3,950,980
[45] Apr. 20, 1976

[54] VAPOR SAMPLING DEVICE

[75] Inventors: David L. Braun, Lake Elmo; John A. Trine, Landfall, both of Minn.

[73] Assignee: Minnesota Mining and Manufacturing Company, St. Paul, Minn.

[22] Filed: Mar. 27, 1974

[21] Appl. No.: 455,211

[52] U.S. Cl. ............................ 73/23; 23/254 R; 338/34
[51] Int. Cl.² ................ G01N 27/04; G01N 31/06
[58] Field of Search ............ 73/23, 27 R; 324/65 R, 324/71 SN; 338/34, 35; 340/237 R; 23/254 E, 232 R, 232 E; 117/212; 264/210

[56] References Cited
UNITED STATES PATENTS

| | | | |
|---|---|---|---|
| 2,976,188 | 3/1961 | Kohl | 117/212 |
| 3,478,574 | 11/1969 | Modell | 73/27 R |
| 3,481,179 | 12/1969 | Howarth | 73/27 R |
| 3,558,764 | 1/1971 | Isaccson et al. | 264/210 F |
| 3,578,409 | 5/1971 | Silverman | 73/27 R X |
| 3,703,696 | 11/1972 | Browall et al. | 338/35 |
| 3,714,562 | 1/1973 | McNerney | 324/65 R |
| 3,755,800 | 8/1973 | Purt et al. | 23/254 E |
| 3,764,269 | 10/1973 | Oldham et al. | 73/23 |
| 3,771,960 | 11/1973 | Kim et al. | 23/254 E |

*Primary Examiner*—James J. Gill
*Assistant Examiner*—Stephen A. Kreitman
*Attorney, Agent, or Firm*—Alexander, Sell, Steldt & DeLaHunt

[57] ABSTRACT

A device for measuring the presence or time-average amounts of at least one selected gas in a mixture thereof which comprises an enclosure having therewithin at least one substance which interacts with the gas to be monitored. Attenuating means associated with the enclosure regulate gas movement within said enclosure to insure that an essentially placid layer of gas exists between the attenuating means and the reactive substance insuring that the amount of selected gas available to react with the interactive substance is basically a function of the concentration of the gas or gases being measured and its diffusion through the placid layer. The amount of selected gas measured is substantially independent of the velocity and impinging angle of the gas mixture at the interface of the enclosure with the ambient gas mixture. The device is capable of controlling mass uptake and response time without losing velocity and angle independence. The control of mass uptake can be accomplished independent of the concentration of detectable gas.

3 Claims, 6 Drawing Figures

VAPOR SAMPLING DEVICE

BACKGROUND OF THE INVENTION

1. Field Of The Invention

In one aspect this invention relates to devices for measuring the presence of selected gas or gases in a gas mixture. In another aspect this invention relates to a device suitable for measuring the time-average exposure of an individual to a selected gas in air.

2. Prior Art

One example of a detection device which measures the presence of a contaminant vapor is U.S. Pat. No. 3,714,562 issued to McNerny which discloses the use of a metallic film to absorb a selected vapor and the presence of the vapor is measured by a change in resistance. Also disclosing resistance-type sensing elements are U.S. Pat. Nos. 3,703,696; 2,976,188 and 2,713,625. These prior art detectors pass a moving vapor over the resistance element making them dependent on a constant velocity for accuracy. Such devices do not function properly when attached to a person such that the gas flow over the sensor is dependent upon the person's movement. Because people have a variation in movement, and the air movement in a room may also vary, a simple badge sensor which permits the access of air to a sensing element when attached to a person, will vary greatly in response as a function of velocity making accurate monitoring of an individual's exposure impossible.

A further detection system is disclosed by Palmes and Gunnison, "Personal Monitoring Device for Gaseous contaminants," *American Industrial Hygiene Association Journal*, V. 34, No. 2, February, 1973, pp. 78–81. This device measures concentrations by measuring the quantity of a selected gas which diffuses through a single orifice of known size into a chamber maintained at zero concentration of the selected gas by means of a collecting medium.

BRIEF SUMMARY OF THE INVENTION

The device of the present invention provides a monitoring device which can measure the presence or time-average exposure of the badge to a selected vapor or gas in a mixture of gases. The device comprises a chamber with an open end and encloses a detector layer for interaction with the vapor to be measured. An attenuating or flow control means regulates bulk gas movement in and out of the chamber and is located within and/or at the entrance to said chamber between the open end and the interactive layer to insure that a placid layer of gas exists between the attenuating means and the interactive layer. This insures that the amount of selected vapor which interacts with the detector layer is a function of diffusion of the selected gas through the placid gas layer and is substantially independent of velocity, direction of flow, turbulence, etc. at the open end of the chamber.

BRIEF DESCRIPTION OF THE DRAWINGS

A further understanding can be had by referring to the accompanying drawing in which.

DETAILED DESCRIPTION OF THE PREFERRED EMBODIMENTS

Figure 2:
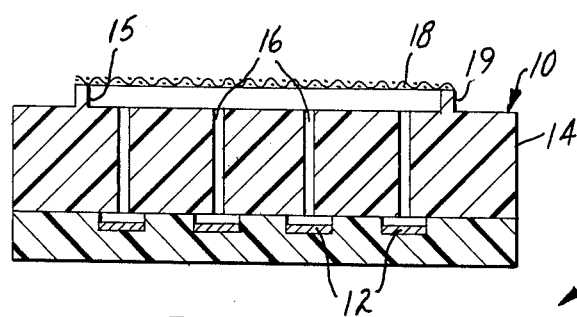
FIG. 2 is a sectional view of FIG. 1 taken along the line 2—2, in assembled form.

In general, it is desirable to control at least three factors in making an acceptable gas sampling device. Ideally, the device should (1) be independent of the effects of ambient velocity; (2) have controllable mass uptake and (3) have controllable response time. The term gas as used herein includes substances dispersed in the molecular or atomic state including those materials which can exist as solids or liquids at normal room temperature and are generally called vapors in their gaseous forms.

In order to demonstrate velocity and air flow direction effects, a mercury gas detector was formed. A device of polystyrene was injection-molded with a serpentine pattern about ⅛ in. (0.32 cm.) wide, 1/32 in. (0.08 cm.) deep and 6 in. (15.24 cm.) in length. A 150 Angstrom thick adherent gold film was vapor deposited on the patterned surface of the substrate and the high portion of surface of the substrate abraded, leaving a thin gold serpentine resistor. A diffusion grating having 36 parallel holes of 0.062 in. (0.16 cm.) diameter by 0.250 in. (0.64 cm.) length in a block of polystyrene was placed over the detector. The holes were uniformly spaced on 0.125 in. (0.32 cm.) centers and perpendicular to and just above the gold detection surface. The devices were tested for velocity dependence at various angles of attack and at various velocities using air having a constant concentration of 50 micrograms Hg/m³ for a period of 25 hours. The attack angle is the acute angle between the direction of flow and the face of the device. The amount of mercury absorbed was determined by the change in the resistance of the gold film. The response of the device is determined by measuring the change in resistance and calculating a "Normal Response" Unit (N). N is calculated by using the formula:

$$5.0 \times 10^2 \left(\frac{\Delta R}{R}\right)\left(\frac{1}{tc}\right)$$

where $R$ is the initial resistance of the strip, $\Delta R$ is the change in resistance after exposure to mercury gas, $t$ is the time of exposure to mercury gas and $c$ is the concentration of mercury gas in mg Hg per cubic meter of air.

TABLE I

| Velocity | Attack Angle | N |
|---|---|---|
| Still air 91.4 cm/sec | (N/A)* | 15.7 |
| 3 ft/sec 91.4 cm/sec | 90° | 15.1 |
| 3 ft/sec 183 cm/sec | 45° | 32.4 |
| 6 ft/sec 183 cm/sec | 90° | 27.9 |

TABLE I-continued

| Velocity | Attack Angle | N |
| --- | --- | --- |
| 6 ft/sec | 45° | 51.4 |

*(N/A) = not applicable

These results indicated that the device response N at normal room velocities of 3 ft/sec (91.4 cm/sec) is unaffected so long as the air flow is parallel to the axis of the holes. Increasing the velocity to 183 cm/sec (a fast walking speed) doubles the responses of the device for parallel flow and about quadruples response for the 45° angle of attack.

The ratio of the response at a 183 cm/sec velocity and a 45° attack angle to the response under stagnant conditions provides a good measure of a monitoring device's freedom from velocity effects. Generally an acceptable device will not have a velocity-dependent variation greater than about ± 45 percent when compared to the still air conditions.

It has been found that the velocity effects can be controlled by an attenuating means which provides a placid layer. The attenuating means allows a diffusional transport of the gas from the ambient atmosphere to the detector layer and provides the device of this invention with the desired response characteristics. The attenuating means can take various forms such as wire screens, porous plates of particulate material, nonwoven batting, microporous polymeric films, etc. Fine woven or microporous polymeric screens are one example of attenuating means which can reduce the velocity effect in a device of this invention and insure a relatively placid layer of gas between the opening of the device's enclosure and the interactive substance contained therein. Fine wire screens, such as 270 mesh and finer, offer little resistance and under some circumstances may increase the diffusion or mass transport of the gas molecules or atoms across the screen's width but can at the same time provide as much as a 300 percent reduction in velocity effects.

A further type of attenuating means is a porous sintered plate or layer made of particulate material. One example of a particulate material is epoxycoated spherical glass beads such as those disclosed in U.S. Pat. No. 3,175,935. The glass beads coated with a heat-bonding epoxy are packed in a mold and the resulting shape heat-cured. During curing, the resin flows to the contiguous points of contact of the spherical glass beads, bonding the glass beads together as a strong, porous material. Also useful are metallic particles which can be compacted and sintered using standard powder metallurgy to form porous plates. Suitable metal particles include copper, brass, bronze, stainless steel as well as other metals and alloys. The porous plate provides a relatively low mass transport attenuating means and also provides an excellent opportunity to screen out interferring gases by placing interacting substances within the plate. The void volume of the porous plate and pore size govern the degree of attenuation and can be changed by mixing the types of particles used, the addition of resin in the case of beads or using a filler which fills a portion of the voids.

The attenuating means and the diffusion grating provide control of the sensitivity of the device by controlling the amount of gaseous material which passes through the means. The porous plates of particulate material will pass only a small fraction of the gas which would impinge on the detector layer is no plate were present or which would be passed by an open placid layer. Thus, the attenuating means provide a method for tailoring the response of the device to different ambient conditions. Where a long-term device is wanted, or where the selected gas is in high concentration, mass transport can be reduced, and where quick short-term response is important or the selected gas is in low concentration, a less restrictive attenuating means can be used.

Control of the response time is a characteristic of the placid layer formed. Atomic and molecular drift from a region of high ambient concentration to a low or zero concentration at the interactive substance occurs at a characteristic drift velocity. The characteristic drift velocity (CDV) is equal to twice the binary diffusion constant divided by the length over which the molecules travel (the length of the concentration gradient). Because the binary diffusion constants of various gases are relatively fixed, the primary control of response time is the length of the concentration gradient. The average time (T) necessary for an atom or molecule to move across a placid layer thickness (L) is a function of the characteristic drift velocity (CDV) and is related to the binary diffusion constant (D) by the expression:

$$T = \frac{L}{CDV} = \frac{L}{2D/L} = \frac{L^2}{2D}$$

Because of the parabolic relationship between the response time and placid layer thickness, the use of a thick placid layer to reduce velocity effects extracts a heavy penalty in response time. In choosing a gradient length which gives the desired response time, the choice of velocity attenuating means will be important in controlling velocity effects especially where, for quick response, a thin placid layer is used.

The interactive substances useful in the practice of this invention include materials which absorb, adsorb, react or otherwise combine with the gas being measured. Where the interactive substance undergoes a physical change, it is possible to measure the amount of material present immediately while other materials which absorb or adsorb the gas being monitored can be analyzed by standard analytical techniques, e.g. gas chromatography. Specific examples include palladium (II) chloride embedded in filter paper which changes color upon absorbing carbon monoxide (white to grey to black), thin metal films (e.g., gold) which change their resistance, exchange resins, absorbers and adsorbers which retain a gas for later gas analysis, liquids or gels which absorb the gas for gravimetric analysis. The interactive substances useful in the practice of this invention will often be specific for a particular gas or class of gases. However, it is possible to use an absorbing material and chromatographic analysis to trap and measure a large number of gaseous components simultaneously.

The enclosure of this invention is constructed of materials which are not reactive with the ambient environment and which are nonreactive and nonabsorbtive with respect to the gas being measured. Examples of such materials are stainless steel, polyethylene, polypropylene, metals, etc. In general, the injection molded plastics form preferred enclosures because of their low expense, chemical inertness and ease of manufacture.

The gas detection device of this invention can be made small, e.g., 2.5 to 5 cm. in width and length, allowing the device to be mounted on the clothing or body of a person. After wearing the badge for a period of time, as the person goes about his normal business, the device can be analyzed. The amount of gas detected divided by the time the device is exposed gives a time average value of exposure in addition to the cumulative exposure of the device.

Figure 1:
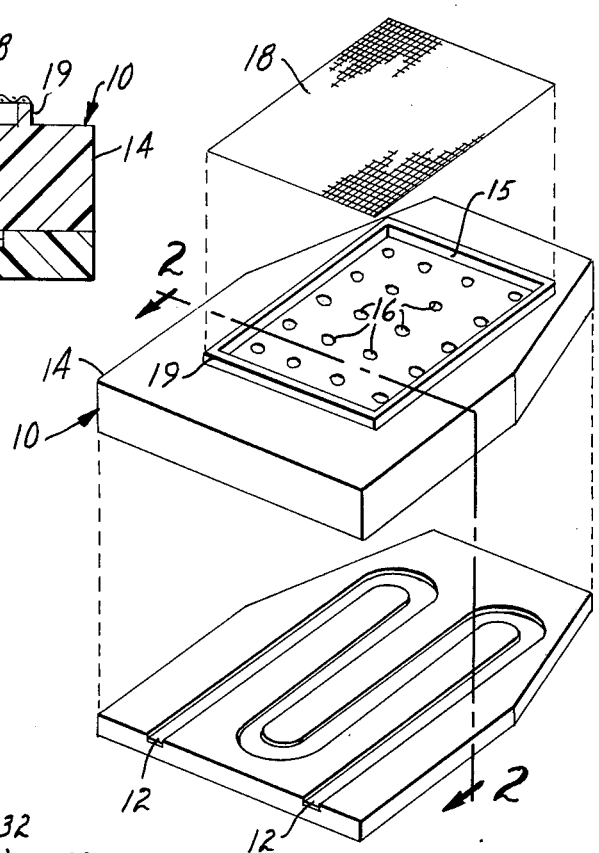
FIG. 1 is an exploded view of a gas detection device with a diffusion grating and a mesh screen in series with the diffusion grating.

Referring to the accompanying drawing in which like numerals refer to like parts, initially to FIGS. 1 and 2, a detection device 10 has a thin gold detector layer 12 suitable for absorbing mercury gas disposed thereon as a serpentine pattern. The detector unit has a diffusion grating 14 disposed thereon, the diffusion grating having a plurality of channel 16 therethrough. A fine woven mesh screen 18 is held above the upper surface of the channels 16 by a lip 19 which encircles the channels and keeps the screen from contacting the upper surface of the diffusion grating. The screen defines a layer 15 of relatively placid gas between the screen 18 and the upper surface of diffusion grating 14, the placid layer serving to shield the diffusion grating from the effects of velocity.

Figure 3:
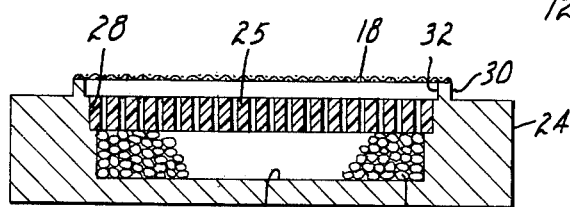
FIG. 3 is a sectional view of a gas detector showing a variation of screen and diffusion grating.
Figure 4:
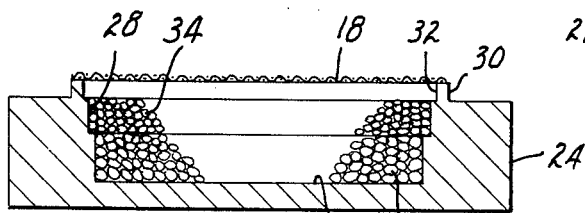
FIG. 4 is a sectional view of a gas detector having a screen and porous plate.

FIGS. 3 to 6 show gas analyzing devices with various attenuating means in series which form placid layers and minimize the effects of velocity. In FIGS. 3 and 4 a fine screen 18 protects the upper surface of an underlying means from the effects of gas moving past the analyzing device.

Figure 6:
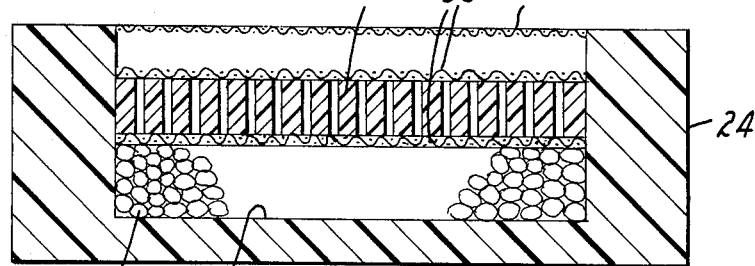
FIG. 6 is a sectional view of a gas detector having multiple screens and a diffusion grating.

Specifically, in FIGS. 3, 4 and 6 an enclosure 24 has a bed 26 of interactive substance contained within a chamber 27 forming a detection layer. In FIG. 3 the open end 28 has a diffusion grating 14 with a plurality of channels therein. A mesh screen 18 is mounted a few millimeters above the diffusion grating 14 attached to the protuberances 30 so that there are no openings to the placid layer larger than the mesh openings. This prevents substantial amounts of gas from entering at the edges of the screens and causing velocity effects. This configuration forms a placid layer of gas 32 between the screen 18 and the diffusion grating 14. This configuration provides a useful detection device and insures that the gas in contact with the upper surface of the diffusion grating is essentially placid. In FIG. 4 the diffusion grating of FIG. 3 has been replaced by a porous plate 34 formed of particulate material which has been consolidated to form a porous structure. The resulting attenuating means transports gas from the ambient surroundings to the interactive substance 26 by diffusion and minimizes velocity effects. In FIG. 6 the device of FIG. 3 has been modified by the addition of screens 36 above and below the diffusion grating 14 for a further reduction in velocity effects.

Figure 5:
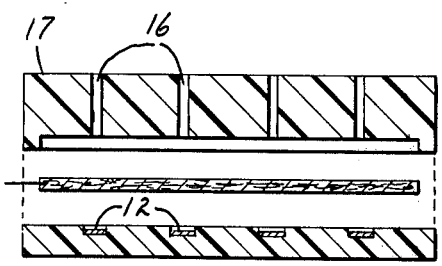
FIG. 5 is an exploded sectional view of a gas detector with a diffusion grating and nonwoven web.

The monitoring device of FIG. 5 has a mat 22 of compressed nonwoven fibers placed between the diffusion grating 14 and the detector 10. The mat 22 serves to further attenuate movement of gas within the diffusion channels. The mat may contain a reactive substance dispersed throughout which traps or holds a particular type of contaminant to avoid poisoning or alteration of the detection layer.

One of the attenuating means may also be used to screen out or absorb one or more gas constituents of the gas mixture which could interfere with the interactive substance of the gas to be measured. For example, where acetone or other organic gases are present, activated carbon in the web 22 of FIG. 5 will absorb the organics present while allowing gas, e.g. $H_2S$, CO and Hg to pass through the attenuating layer.

The invention is further illustrated by reference to the following nonlimiting examples in which all parts are by weight unless otherwise specified. Where a particular item does not apply to an individual sample, the symbol N/A appears in the tabulated results.

EXAMPLE 1

The diffusion grating used in the specification to generate Table I was modified by placing a fine porous mesh of woven stainless steel mesh (such as used for sifting fine particles) over the parallel holes. The mesh openings were 0.0053 cm. on a side and the open area of the mesh was 32 percent. This device was tested for velocity dependence at a constant mercury vapor concentration as described hereinbefore with respect to Table I.

TABLE II

| Velocity | Attack Angle | N |
|---|---|---|
| Still air | (N/A) | 16.4 |
| 183 cm/sec | 90° | 19.5 |
| 183 cm/sec | 45° | 23.6 |

These results show a velocity dependence of 23.6/16.4 = 1.44 compared to 51.4/15.7 = 3.27 for the device of Table I. Since most drafts in rooms where toxic gases might be found are well below 183 cm/sec, the error of the device of this example due to the velocity of the gas would generally be considerably below 44 percent, in most cases less than 20 percent. A slight over-emphasis of the presence of toxic gases is perhaps valuable to those exposed and is acceptable in a personal monitoring device.

Example 2

Water vapor detection devices were made by forming a circular chamber about 0.63 cm. deep and 7.62 cm. in diameter in a block of aluminum. The chamber was filled with "Drierite" (anhydrous $CaSO_4$) and a diffusion grating of "Plexiglass" (polymethylmethacrylate) having 275 holes of 0.062 in. (0.157 cm) diameter by 0.25 in. (0.635 cm) long was sealed over the chamber. A woven screen of polyester monofilament having 0.0017 in. (0.0043 cm) openings and 27 percent open area was suspended 0.3 in. (0.76 cm) above the holes so as to provide a layer of air adjacent to the diffusion grating. The screen was sealed about its perimeter. Thus, a velocity dissipating layer was formed in series with the placid layer formed by the diffusion grating.

The devices were placed in a test chamber at 17 gm. $H_2O/m^3$ of air for 3.17 hr. and the response of the device was measured gravimetrically. The relative weight gain was the percentage of weight gain over the original weight of dessicant.

TABLE III

| Velocity | Attack Angle | Relative Water Gain |
|---|---|---|
| Still air | (N/A) | 9.94 |
| 178 cm/sec | 45° | 11.80 |

These results show a velocity dependence ratio of 11.80/9.94 = 1.19 which represents about 20 percent increase with velocity as compared with 44 percent for Example 1.

EXAMPLE 3

The device of Example 1 was provided with a porous frit in place of the diffusion grating. The porous frit material is made using resin coated glass beads compacted and bonded together, the beads being those described in U.S. Pat. No. 3,175,935. The frit contained closely packed 0.018 in. (0.046 cm) diameter spheres. Volume not occupied by the beads was about 30 percent. Such an inert frit is an excellent attenuating means where chemical activity of the gas is a problem. The result of testing as in Example 1 is tabulated in Table IV.

TABLE IV

| Velocity | Angle | N |
| --- | --- | --- |
| 1.52 cm/sec | (N/A) | 11.69 |
| 183 cm/sec | — | 14.1 |

It is noted that the velocity dependence ratio for frit material is 1.21.

EXAMPLE 4

An enclosure was made 3 in. (7.62 cm) long by ¼ in. (0.63 cm) wide block of "Teflon" having a cavity, the cavity being filled with a small bed of "Witco" Grade 235-12 30 mesh activated charcoal. A nylon diffusion grating having 12 parallel holes of 0.125 in. (0.32 cm) diameter and 0.6875 in. (1.75 cm) length was placed over the cavity. A 200 mesh nickel screen was placed over the entrance of the holes of the diffusion grating. These devices were tested in air at 22°C. saturated with benzene for 0.1 hr. in comparison to comparable devices without screens. The devices with screens responded by an average weight gain of 3.8 mg. benzene and those without screens responded by 3.03 mg. The fact that the 200 mesh screen is only about 47 percent open clearly has not reduced the mass uptake by the same amount. Quite the opposite, surprisingly, the screen increased the response. It was concluded that the presence of the fine porous screen does not reduce mass uptake as may have been expected.

EXAMPLE 5

In order to verify the result of Example 4, the placid layer means of Example 2 were tested in parallel to the placid layer means of Example 1. Under exposure to Hg vapor at still air conditions, the average response of devices with the fine porous media was 16.4. The average response of those without the media was 14.0. The ratio of response of screened to unscreened devices is greater than one. Thus, the unusual result of Example 5 is borne out and the presence of a fine porous media may increase the response slightly instead of decreasing it as might have been expected.

EXAMPLE 6

To measure organic vapor concentration, a molded polypropylene enclosure having a lower chamber 0.50 in. diameter and 0.070 in. deep was formed. About 100 milligrams of "Witco" 18 × 40 U.S. mesh AC-4259 activated charcoal was placed into the chamber. A stainless steel screen such as that of Example 1 was placed over the chamber to hold the carbon in place. A diffusion grating having 12 evenly spaced channels 0.062 in. diameter and 0.108 in. length was placed atop the stainless screen and the woven polyester screen of Example 2 was bonded over the channel entrances.

The devices were exposed to individual and mixed concentrations of toluene, trichloroethylene and methylethyl ketone (MEK) vapors for periods of time. The results are summarized below:

| TEST | VELOCITY cm/sec | ANGLE° | VAPOR(s) | TIME Hr. | CONCENTRATION mg/m³ | CALCULATED STILL AIR MASS UPTAKE (mg) | OBSERVED MASS UPTAKE (mg) |
| --- | --- | --- | --- | --- | --- | --- | --- |
| 1 | 76.2 | 90 | Toluene | 2 | 483 | 0.202 | 0.220 |
| 2 | 76.2 | 45 | Toluene | 2 | 483 | 0.202 | 0.221 |
| 3 | 76.2 | 90 | Trichloro-ethylene | 1 | 1146 | 0.253 | 0.250 |
| 4 | 76.2 | 90 | MEK | 0.67 | 984 | 0.151 | 0.17 |
| 5 | 76.2 | 90 | MEK | 1.75 | 313 | 0.129 | 0.13 |
|  |  |  | Trichloro-ethylene | 1.75 | 598 | 0.219 | 0.21 |
|  |  |  | Toluene | 1.75 | 253 | 0.098 | 0.08 |

The velocity dependence in tests 1 through 4 was a maximum of 12.5 percent. This is a good result even though the test conditions were not as severe as in previous examples.

In this example, diffusion of organic vapors through the placid layer, about 0.27 cm., results in a diffusion time of about 0.5 seconds for most organic vapors. The velocity independence of the device of this example was good despite the narrow placid layer.

EXAMPLE 7

The mercury detection device described in connection with Table I was provided with a grating having four rectangular slots 0.125 in. (0.31 cm) wide, 0.25 in. (0.64 cm) deep and 1.05 in. (2.66 cm) long. The upper surface of the grating was covered by a micro-porous polypropylene film available as "Celgard 2400," the film being described in U.S. Pat. No. 3,558,764 the disclosure of which is incorporated herein by reference. The pores of the "Celgard" are generally believed to be 0.1 micron or less and to represent about 35 percent of the surface area of the film.

Testing as in Example 1 at stagnant conditions N = 45.1 and at 45° attack angle and 183 cm/sec velocity N = 51.7. The device increased its response only 14 percent even under the effects of velocity and provides a highly responsive device with only minimal velocity dependence.

What is claimed is:

1. Device useful for measuring the amounts of at least one selected vapor in an ambient gas mixture, comprising:
   a flat substrate having a shallow cavity therein;

a flat, elongated detector layer capable of interacting with the vapor to be measured contained within, coextensive with and in contact with the bottom of said cavity;

multiple flat, porous gas-flow attenuating layers superimposed on, and overlying each other, said cavity and said detector layer and being substantially coextensive with said substrate, at least one of said gas-flow attenuating layers being spaced a short distance apart from and parallel to said detector layer or from another one of said gas-flow attenuating layers so as to form layers of substantially placid gas between all of the layers of said device, whereby the effect of turbulence, velocity of movement or other disturbance in the ambient gas mixture is minimized and the amount of vapor to be measured is caused to be a function of diffusion through the said thin layer of placid gas and is substantially independent of velocity of the ambient gas mixture at the interface between the device and the ambient gas mixture.

2. Device according to claim 1 wherein the detecting layer is selected from the group consisting of activated charcoal, gold, palladium (II) chloride and anhydrous calcium sulfate.

3. Device according to claim 1 wherein the gas flow attenuating layers are selected from the group consisting of porous glass frits, fine wire screens, woven or microporous polymeric films, porous plates of particulate material, nonwoven batting and combinations thereof.

* * * * *